(12) United States Patent
Tamura

(10) Patent No.: US 8,882,675 B2
(45) Date of Patent: Nov. 11, 2014

(54) METHODS AND APPARATUS FOR ULTRASOUND IMAGING

(75) Inventor: Tadashi Tamura, North Haven, CT (US)

(73) Assignee: Hitachi Aloka Medical, Ltd., Tokyo (JP)

( * ) Notice: Subject to any disclaimer, the term of this patent is extended or adjusted under 35 U.S.C. 154(b) by 199 days.

(21) Appl. No.: 12/717,428

(22) Filed: Mar. 4, 2010

(65) Prior Publication Data

US 2011/0015526 A1 Jan. 20, 2011

Related U.S. Application Data

(60) Provisional application No. 61/226,053, filed on Jul. 16, 2009.

(51) Int. Cl.
*A61B 8/00* (2006.01)
*G01S 7/52* (2006.01)
*A61B 8/06* (2006.01)
*G01S 15/89* (2006.01)
*A61B 8/08* (2006.01)

(52) U.S. Cl.
CPC . *A61B 8/06* (2013.01); *A61B 8/461* (2013.01); *G01S 7/52071* (2013.01); *G01S 15/8981* (2013.01); *A61B 8/0883* (2013.01); *A61B 8/0891* (2013.01)
USPC ............ 600/453; 600/447; 600/449; 600/451

(58) Field of Classification Search
USPC .......................... 600/437, 440, 441, 453–457
See application file for complete search history.

(56) References Cited

U.S. PATENT DOCUMENTS 5,027,122 A 6/1991 Wieler
5,383,463 A * 1/1995 Friedman ...................... 600/455
(Continued)

FOREIGN PATENT DOCUMENTS

JP H0549639 A 3/1993
JP 2001224592 A 8/2001
(Continued)

OTHER PUBLICATIONS

M. Wuest et al., "A Variational De-Aliasing Technique", 2000, Phys. Chem. Earch (b), vol. 25, No. 10-12, Copyright 2000 Eisevier Science Ltd., PII: S1464-1909(00)00175-1, (pp. 1179-1183, total 5pgs.).

(Continued)

*Primary Examiner* — Tse Chen
*Assistant Examiner* — Mark Remaly
(74) *Attorney, Agent, or Firm* — Buckley, Maschoff & Talwalkar LLC

(57) ABSTRACT

Some embodiments include acquisition of color Doppler data, detection of one or more transitions of the color Doppler data, each of the one or more transitions being between a first area representing flow velocity in a first direction and a second area representing flow velocity not in the first direction, and application of a first set of aliasing corrections to the color Doppler data to generate second color Doppler data. For each of the one or more transitions, a first energy function is calculated based on the one or more pairs of color Doppler values in the second color Doppler data, and a first total energy function associated with the first set of aliasing corrections is determined based on the calculated first energy functions. Next, a second total energy function associated with a second set of aliasing corrections is determined based on calculated second energy functions.

18 Claims, 12 Drawing Sheets

(56) References Cited

U.S. PATENT DOCUMENTS

| | | | |
|---|---|---|---|
| 7,044,913 B2 * | 5/2006 | Shiki | 600/454 |
| 2003/0125624 A1 | 7/2003 | Shiki | |
| 2006/0184032 A1 | 8/2006 | Shiki | |

FOREIGN PATENT DOCUMENTS

| | | | |
|---|---|---|---|
| JP | 2003061958 A | 3/2003 |
| JP | 2004164479 A | 6/2004 |
| WO | 2008/123596 A1 | 10/2008 |

OTHER PUBLICATIONS

PCT International Search Report, dated Feb. 11, 2010 (Nov. 2, 2010), for PCT International Application No. PCT/JP2010/062294, 4pgs.

Hitachi Aloka Medical, Ltd., Japanese Office Action, dated Mar. 11, 2014, for Japanese Patent Application No. 2012-502047, entitled: Methods and Paratus for Ultrasound Imaging, 4pgs.

Hitachi Aloka Medical, Ltd., "Japanese Office Action", dated Jul. 1, 2014, for Japanese Patent Application No. 2012-502047, entitled: Methods and Paratus for Ultrasound Imaging, 3pgs.

* cited by examiner

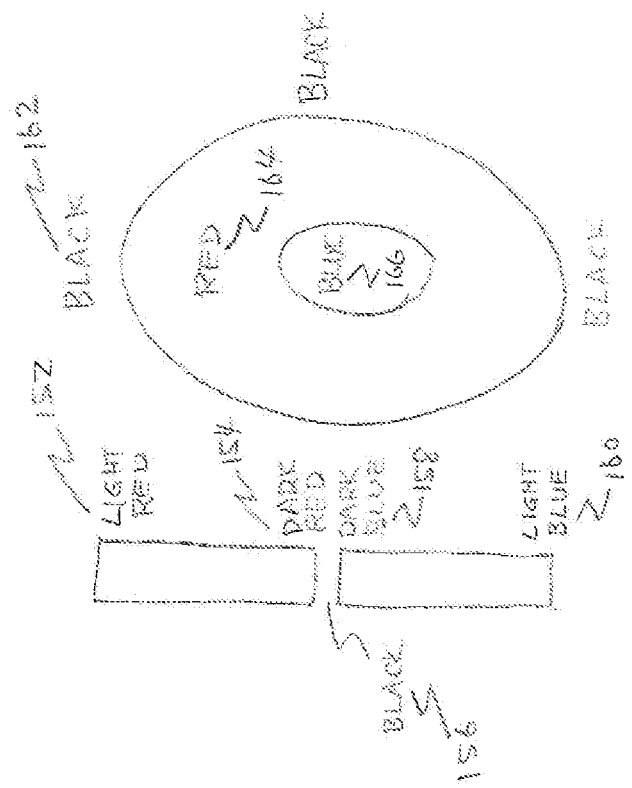
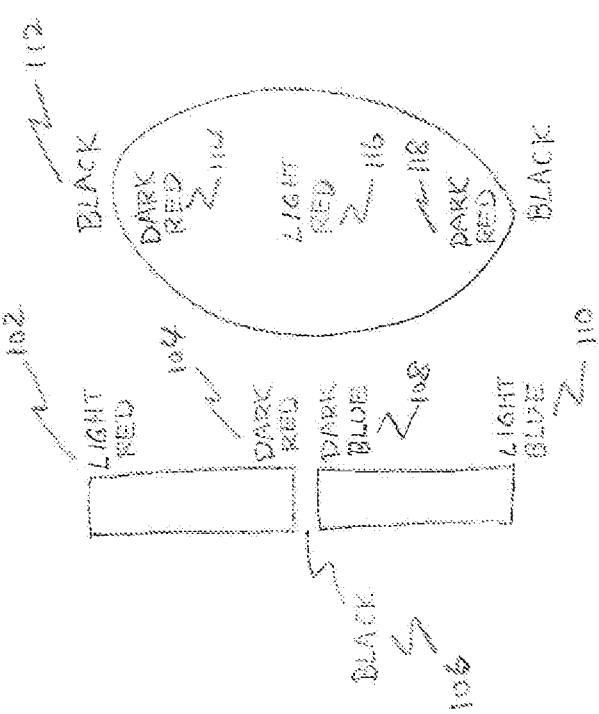

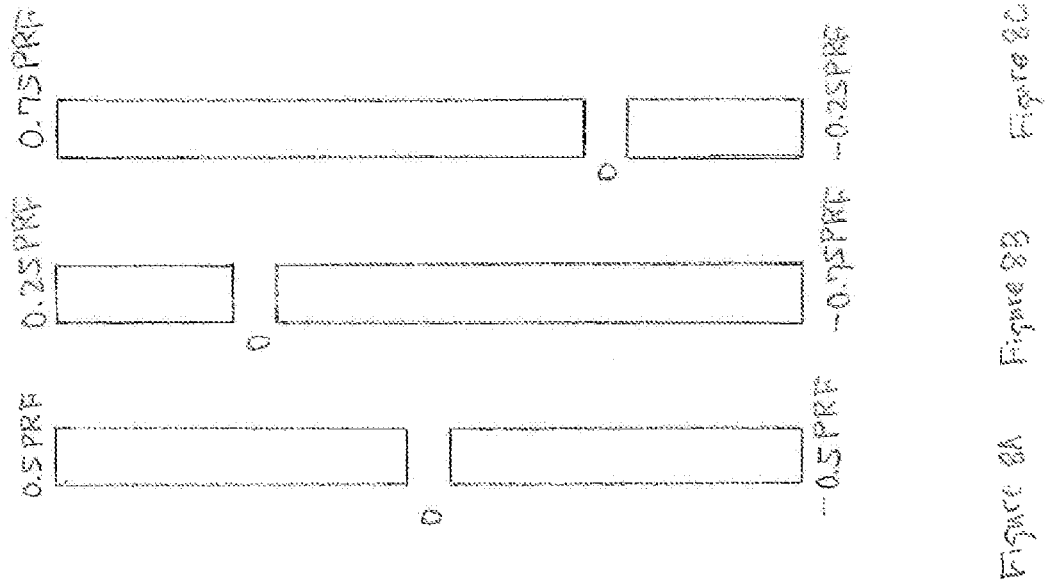

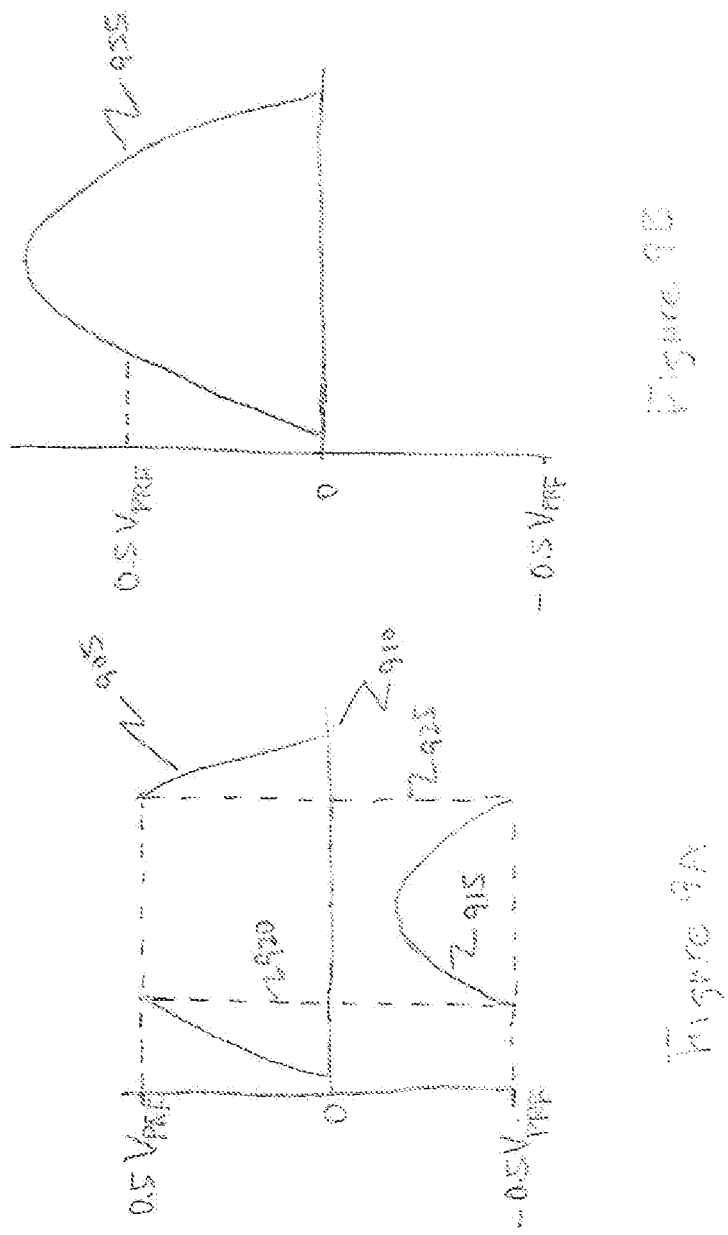

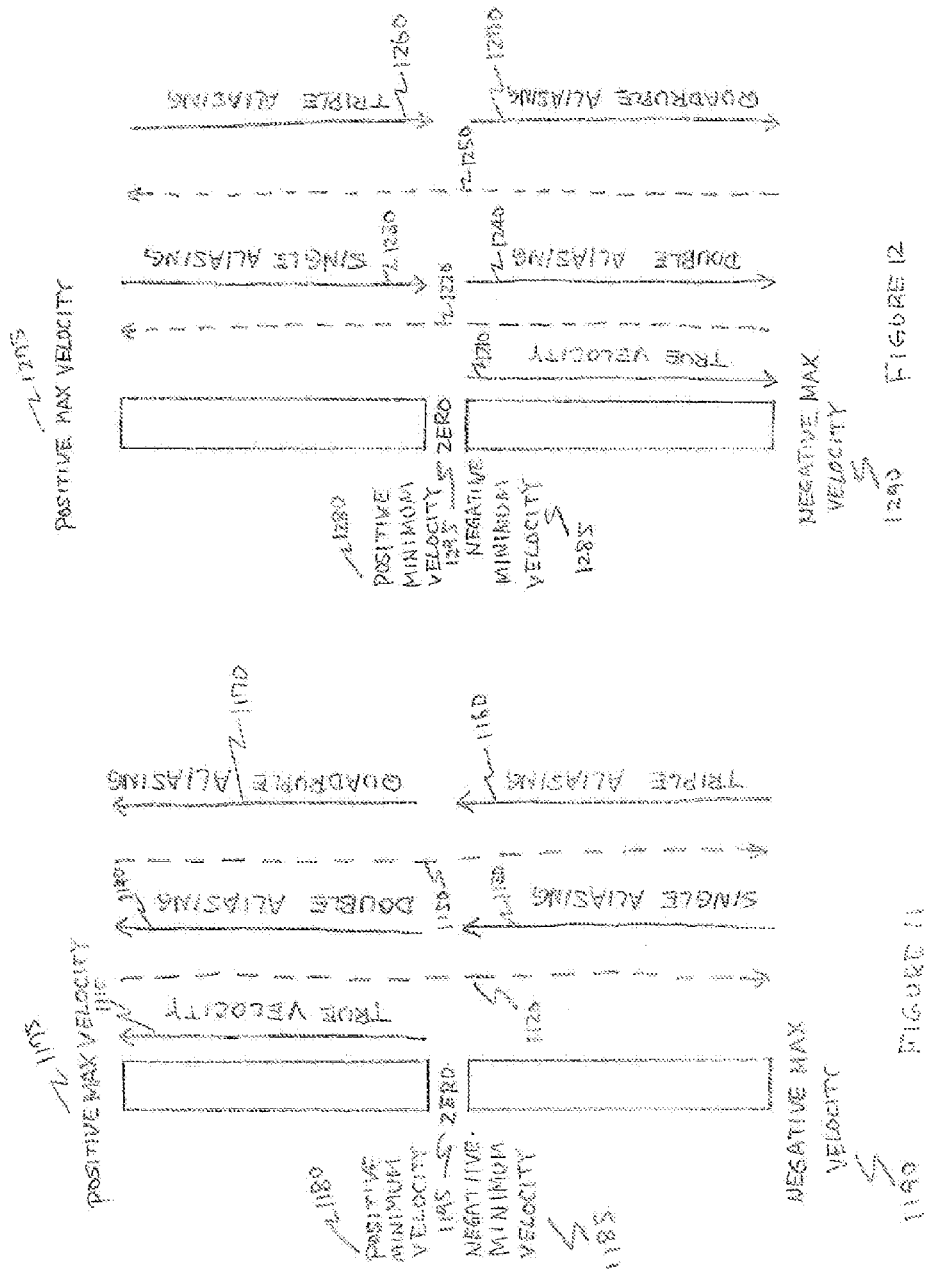

METHODS AND APPARATUS FOR ULTRASOUND IMAGING

CROSS-REFERENCE TO RELATED APPLICATION

The present application claims priority to U.S. Provisional Patent Application Ser. No. 61/226,053, filed on Jul. 16, 2009 and entitled "Method and Apparatus for Ultrasound Imaging", the contents of which are incorporated herein by reference for all purposes.

BACKGROUND

Systems and methods described herein generally relate to the field of ultrasound imaging. More specifically, embodiments described below relate to methods and systems for color flow imaging.

Ultrasound is used to image various internal structures, including but not limited to the heart, the liver, a fetus, and blood vessels. For diagnosis of cardiovascular diseases, color Doppler (or color flow) imaging is usually used to visualize blood flow in the heart or blood vessels. Abnormal conditions often increase blood flow velocity in comparison to that under normal conditions. The increased velocity may result in aliasing within a corresponding color Doppler image. Color Doppler uses a pulse ultrasound technology for its spatial sampling capability, which limits the maximum velocity which can be detected without experiencing aliasing. The pulse repetition frequency (PRF), which is also the sampling frequency, sets the maximum frequency limitation. This limitation, in turn, limits the maximum blood flow velocity which can be measured without exhibiting aliasing. This limitation may be particularly problematic in cardiac cases. For example, the PRF cannot be set high enough to measure abnormally high blood velocities that occur at substantial imaging depths such as, for example, regurgitation jets across heart valves. Therefore, under abnormal cardiac conditions, color Doppler often exhibits aliasing, thereby reducing the reliability of any diagnosis based on the blood flow image. Thus, there exists a need to address this aliasing problem.

SUMMARY

Some embodiments include acquisition of color Doppler data, detection of one or more transitions of the color Doppler data, each of the one or more transitions being between a first area representing flow velocity in a first direction and a second area representing flow velocity not in the first direction, and application of a first set of aliasing corrections to the color Doppler data to generate second color Doppler data.

For each of the one or more transitions, one or more pairs of color Doppler values in the second color Doppler data, which are located on opposite sides of the transition, are determined. Also, for each of the one or more transitions, a first energy function is calculated based on the one or more pairs of color Doppler values in the second color Doppler data which are located on opposite sides of the transition, and a first total energy function associated with the first set of aliasing corrections is determined based on the calculated first energy functions.

Next, a second set of aliasing corrections is applied to the color Doppler data to generate third color Doppler data and, for each of the one or more transitions, one or more pairs of color Doppler values in the third color Doppler data, which are located on opposite sides of the transition, are determined. A second energy function is calculated for each of the one or more transitions based on the one or more pairs of color Doppler values in the third color Doppler data which are located on opposite sides of the transition, and a second total energy function associated with the second set of aliasing corrections is determined based on the calculated second energy functions.

BRIEF DESCRIPTION OF THE DRAWINGS

FIG. 1A: Color Doppler image.
FIG. 1B: Color Doppler image with two flow areas.
FIG. 8A: Color-coded Doppler shift frequency (velocity) scale with no baseline shift.
FIG. 8B: Color-coded Doppler shift frequency (velocity) scale with a baseline shift of $$\frac{f_{PRF}}{4}.$$

FIG. 8C: Color-coded Doppler shift frequency (velocity) scale with a baseline shift of $$-\frac{f_{PRF}}{4}.$$

FIG. 9A: Color Doppler velocity distribution across a vessel with aliasing.
FIG. 9B: Color Doppler velocity distribution across a vessel with aliasing correction.
FIG. 11: Diagram of velocity aliasing of various degrees in the positive velocity direction.
FIG. 12: Diagram of velocity aliasing of various degrees in the negative velocity direction.

DETAILED DESCRIPTION

Figure 2B:
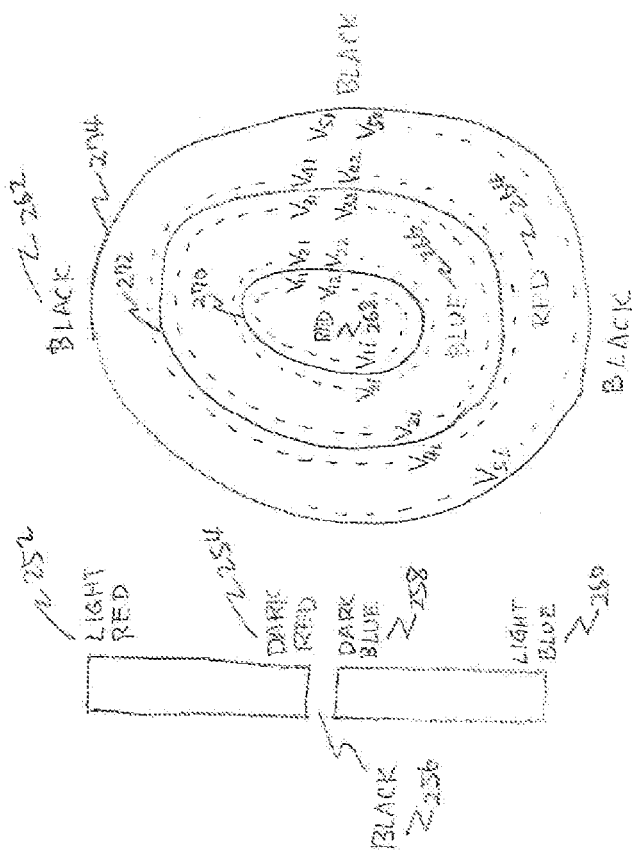
FIG. 2B: Color Doppler image with three flow areas.

Embodiments will be described with reference to the accompanying drawing figures wherein like numbers represent like elements throughout. Before embodiments of the invention are explained in detail, it is to be understood that embodiments are not limited in their application to the details of the examples set forth in the following description or illustrated in the figures. Other embodiments may be practiced or carried out in a variety of applications and in various ways. Also, it is to be understood that the phraseology and terminology used herein is for the purpose of description and should not be regarded as limiting. The use of "including," "comprising," or "having," and variations thereof herein is meant to encompass the items listed thereafter and equivalents thereof as well as additional items. The terms "mounted," "connected," and "coupled," are used broadly and encompass both direct and indirect mounting, connecting, and coupling. Further, "connected," and "coupled" are not restricted to physical or mechanical connections or couplings.

It should be noted that embodiments are not limited to any particular software language described or that is implied in the figures. One of ordinary skill in the art will understand that a variety of alternative software languages may be used for implementation of some embodiments. It should also be understood that some of the components and items are illustrated and described as if they were hardware elements, as is common practice within the art. However, one of ordinary skill in the art, and based on a reading of this detailed description, would understand that, in at least one embodiment, components in the method and system may be implemented in software or hardware.

An ultrasound transducer transmits ultrasound (i.e., ultrasonic waves) into a human body to image various internal structures, including but not limited to blood vessels, a fetus, and the heart. Scatterers in tissue scatter the ultrasound and the scattered ultrasound is returned to the transducer. A receive beamformer creates ultrasound beams and a postprocessor creates an image of tissues from the amplitude of the returned ultrasound signal as a B-mode image.

Blood vessels or the heart are often imaged, since they indicate cardiovascular conditions of patients. Blood flow information is usually acquired using color Doppler and spectral Doppler techniques.

Color Doppler is a two-dimensional imaging technique commonly used for imaging blood flow by sending ultrasonic waves into the blood flow and detecting the scattered ultrasound from the moving red cells. It consists of many beams similar to a B-mode image. A description of a color Doppler technique now follows; embodiments are not limited to the specific details therein.

In order to detect flow velocity, an ultrasound transducer transmits ultrasound signals several times per position to detect motion. To create a two-dimensional flow image, the transmit position is shifted by sub-millimeters, or about the order of an ultrasound wavelength. The transmit position shifting is repeated about 100 times to cover several centimeters and to create a two-dimensional flow image in linear and convex formats. For a phased array transducer or a sector image format, the transmit direction is changed a small angle, for example, about 0.5-1.0 degrees. This is repeated approximately 100 times to cover about 90 degrees of a sector image. For each transmit position or direction, ultrasound is transmitted several times. Received beamformed RF ultrasound signals undergo quadrature demodulation resulting in complex, Doppler I-Q signals.

In a color Doppler technique, the ultrasound is transmitted at a pulse repetition frequency (PRF) and the blood flow velocity is detected as the shift in frequency (Doppler shift frequency) in the received ultrasound signal. The received ultrasound is mixed with in-phase (0 degrees) and quadrature (90 degrees) reference signals of the same frequency as the transmit ultrasound frequency. After low-pass filtering high frequency components (e.g., second harmonics), only the baseband signals are obtained. Wall filtering (i.e., high-pass filtering) is applied to the baseband signals to remove strong clutter noise from tissue and slowly moving tissues such as blood vessel walls, resulting in complex I-Q Doppler signals.

The wall filtering is performed because the Doppler I-Q signals may contain blood flow signal components as well as stationary tissue signal components. The stationary components are typically 30-40 dB greater than the blood flow components. Therefore, it is desirable to reduce or eliminate the stationary signal components in order to detect blood flow accurately.

Generally, the wall-filtered complex I-Q signal is used to derive the Doppler shift frequency because the Doppler shift frequency and the blood velocity have the following relationship $$\Delta f = \frac{2 f_t v \cos\theta}{c}, \quad (1)$$

where $\Delta f$ is the Doppler shift frequency, $f_t$ is the transmitted frequency, v is the blood velocity, $\theta$ is the angle between the ultrasound beam direction and the velocity vector, and c is the speed of sound. The Doppler shift frequency is thus dependent on the angle between the velocity direction and the ultrasound beam direction and is a measurement that an ultrasound color Doppler system may obtain. Velocity (also called flow velocity, color velocity, color flow velocity, color Doppler velocity and others) derived from the Doppler shift frequency is usually the velocity component (i.e. v cos $\theta$) in the ultrasound beam direction or the projection of true flow velocity v onto to the ultrasound beam direction unless the angle is known or measured and corrected accordingly.

In the case of color Doppler, the number of the sampled signals may be limited to 10. Therefore, an auto-correlation technique is usually used to determine the phase differences between the wall-filtered I-Q signal and then to determine the Doppler shift frequency and the blood flow velocity as follows. The color Doppler's I-Q signals z(m)=x(m)+jy(m) are used to calculate "auto-correlation" R as shown in the following equation, where z(m) is the wall-filtered complex I-Q Doppler signal, x(m) is the in-phase (real) signal, y(m) is the quadrature phase (imaginary) signal, m indicates the signal number, j is the imaginary unit and * indicates the complex conjugate.

$$R = \Sigma z(m) \cdot z^*(m-1) \quad (2)$$

The real (Re al(R)) and imaginary (Im ag(R)) parts of R are used to obtain the phase $\phi$ as shown in the following equation.

$$\varphi = \tan^{-1} \frac{\text{Im} ag(R)}{\text{Re} al(R)} \quad (3)$$

Since $\tan^{-1}$ usually provides only $-0.5\pi$ to $0.5\pi$, the position of complex value R in the complex coordinate may be also used to derive $\phi$ in the range of $-\pi$ to $\pi$. The phase (i.e., color Doppler phase) $\phi$ is then related to the Doppler shift frequency as shown in the following equation.

$$\Delta f = \frac{\varphi f_{PRF}}{2\pi} \quad (4)$$

As shown in equation 4, a color Doppler phase of $2\pi$ corresponds to a Doppler shift frequency of the pulse repetition frequency $f_{PRF}$. Or a color Doppler phase of $\pi$ corresponds to a Doppler shift frequency of $$\frac{1}{2} f_{PRF}$$

while a color Doppler phase of $-\pi$ corresponds to a Doppler shift frequency of $$-\frac{1}{2} f_{PRF}.$$

A flow velocity (color flow velocity) in the positive direction corresponds to a positive Doppler shift frequency and a positive color Doppler phase while a flow velocity (color flow velocity) in the negative direction corresponds to a negative Doppler shift frequency and a negative color Doppler phase. Other techniques can be used to obtain the phase and the Doppler shift frequency and the blood flow velocity. The Doppler shift frequency indicates the blood flow velocity. Additionally, the power of the high-pass filtered Doppler I-Q signals indicates the existence of blood flow and the variance of the data indicates turbulence.

Because the color Doppler signals are obtained by the pulsed ultrasound (and also sampling) technique, sampling theory dictates a maximum frequency limit. The maximum frequency is generally half of the pulse repetition frequency (PRF) or $f_{PRF}$. Since the autocorrelation is performed on the complex I-Q Doppler signals, blood flow velocity in a negative direction appears in the negative frequency domain. Therefore, the color Doppler frequency includes negative frequencies that correspond to negative velocities (i.e., velocities having a direction away from the ultrasound transducer). For example, the Doppler shift frequency usually has a range of $$-\frac{f_{PRF}}{2} \text{ to } \frac{f_{PRF}}{2},$$

which in turn corresponds to a range of negative and positive (i.e., velocities having a direction towards the ultrasound transducer) maximum velocities.

Some embodiments employ other Doppler shift frequency ranges. For example, the range may incorporate a "baseline shift" in which the center frequency of the range is not equal to zero. In some embodiments, the baseline shift may be selected from a range of frequencies between $$-\frac{f_{PRF}}{2} \text{ and } \frac{f_{PRF}}{2}.$$

In a particular example as shown in FIG. 8C, a Doppler shift frequency range of $$-\frac{f_{PRF}}{4} \text{ to } \frac{3 f_{PRF}}{4}$$

reflects a baseline shift of $$-\frac{f_{PRF}}{4}.$$

This Doppler frequency range is associated with a negative maximum velocity corresponding to $$-\frac{f_{PRF}}{4}$$

and a positive maximum velocity corresponding to $$\frac{3 f_{PRF}}{4}.$$

Similarly, a Doppler shift frequency range of $$-\frac{3 f_{PRF}}{4} \text{ to } \frac{f_{PRF}}{4}$$

reflects a baseline shift of $$\frac{f_{PRF}}{4}$$

as shown in FIG. 8B. This Doppler frequency range is associated with a negative maximum velocity corresponding to $$-\frac{3 f_{PRF}}{4}$$

and a positive maximum velocity corresponding to $$\frac{f_{PRF}}{4}.$$

In FIG. 8A, the baseline (i.e., 0 Hz) is in the center of the Doppler shift frequency (velocity) scale. When the baseline is shifted, e.g. by $$\frac{f_{PRF}}{4}$$

as shown in FIG. 8B, the positive maximum frequency becomes $$\frac{f_{PRF}}{4}$$

while the negative maximum frequency becomes $$-\frac{3f_{PRF}}{4}.$$

If the baseline shift is $$-\frac{f_{PRF}}{4},$$

the positive maximum frequency becomes $$\frac{3f_{PRF}}{4}$$

while the negative maximum frequency decreases to $$-\frac{f_{PRF}}{4}$$

as shown in FIG. 8C. In other words, the positive maximum frequency is decreased by the baseline shift while the absolute magnitude of the negative maximum frequency is increased by the baseline shift.

Often in cardiovascular applications, as well as in other applications, blood velocities may exceed these maximum velocities, resulting in aliasing. Color Doppler imaging uses color coding methods to display blood velocities (or corresponding Doppler shift frequencies) in colors. With respect to FIG. 1A, the positive velocities may be displayed in shades of red, with higher positive velocities represented by lighter red and lower positive velocities represented by darker red, while the negative velocities may be displayed in shades of blue, with higher negative velocities represented by lighter blue and lower negative velocities represented by darker blue as shown in the color coding bars in the left hand side of FIG. 1A. The positive maximum velocity is represented by light red color 102 while the negative maximum velocity is represented by light blue color 110. The positive minimum velocity is represented by dark red color 104 while the negative minimum velocity is represented by dark blue color 108. Black 106 represents zero velocity. Other color coding methods can be used to represent blood flow velocities.

A color flow image in the right hand side of FIG. 1A includes shades of red including light red 116 in the center and dark red 114, 118 at the top and bottom and apparently is not aliased.

When aliasing occurs, the color flow image may "wrap around" at velocities corresponding to the positive maximum frequency, with velocities corresponding to frequencies which exceed the positive maximum frequency represented by colors associated with negative velocities (e.g., shades of blue). Conversely, aliasing may cause velocities corresponding to frequencies which exceed (in absolute value) the negative maximum frequency to be represented by colors associated with positive velocities (e.g., shades of red). Aliasing therefore complicates the blood velocity image and makes any diagnosis based thereon difficult. FIG. 1B, for example, shows a color flow image which most likely exhibits aliasing. The center area is colored by shades of blue 166 and surrounded by an area of shades of red 164 which is in turn surrounded by areas of black 162. In this case, the center flow area of shades of blue 166 is most likely aliased.

In some embodiments, aliased velocities are detected and corrected as follows. With reference to FIG. 2A, flow velocities (e.g., $V_{11}, V_{12} \ldots$) are obtained by color Doppler near a transition 218 from shades of red 214 (positive velocities) to shades of blue 216 (negative velocities). $V_{11}, V_{12}, \ldots V_{1i}$ are on the blue color side of the transition and are sampled at an equal spatial distance while $V_{21}, V_{22}, \ldots V_{2i}$ are on the red side of the transition and sampled at an equal spatial distance. $V_{1i}$ and $V_{2i}$ may be very close to each other across the transition 218, where i may be between 1 and n. In some embodiments, velocities are sampled at unequal spatial distances.

The following energy function (5) across the transition is then calculated. As shown, the function determines the sum of the absolute velocity differences across the transition.

$$\sum_{i=1}^{n} |V_{1i} - V_{2i}|, \quad (5)$$

where n is the number of velocity samples.

The energy function (5) may be replaced by the following power function (6) or the sum of the p-th power of the absolute differences of velocities (7).

$$\sum_{i=1}^{n} (V_{1i} - V_{2i})^2 \quad (6)$$

or $$\sum_{i=1}^{n} |V_{1i} - V_{2i}|^p \quad (7)$$

Flow velocities (e.g., $V_{31}, V_{32}, \ldots V_{3i}$) are also obtained near the transition from red colors (positive velocities) to black (zero velocities). Since the velocities associated with the black area are zero, an energy function may be obtained as follows, $$\sum_{i=1}^{n2} |V_{3i}|, \quad (8)$$

where n2 is the number of velocity samples. All of the energy functions determined for the FIG. 2A color flow image are linearly summed to create a total energy function. For example, $$\sum_{i=1}^{n} |V_{1i} - V_{2i}| + \sum_{i=1}^{n2} |V_{3i}|. \quad (9)$$

In an alternate embodiment, (9) may be replaced by the following energy function (10), in which the energy functions associated with each transition are weighted with weights $w_1$ and $w_2$.

$$w_1 \sum_{i=1}^{n} |V_{1i} - V_{2i}| + w_2 \sum_{i=1}^{n2} |V_{3i}| \qquad (10)$$

Next, it is assumed that some contiguous area of a single flow direction is aliased. For example, it may be assumed that the blue area in FIG. 2A is aliased. Each velocity of the assumed-to-be-aliased area is corrected by adding a velocity ($V_{PRF}$) corresponding to a Doppler shift frequency of the pulse repetition frequency if the aliased velocity is negative or by subtracting a velocity ($V_{PRF}$) corresponding to a Doppler shift frequency of the pulse repetition frequency if the aliased velocity is positive. In the case of FIG. 2A, $V_{1i}$ are replaced by $V_{1i}+V_{PRF}$ and the total energy function becomes $$\sum_{i=1}^{n} |V_{1i} + V_{PRF} - V_{2i}| + \sum_{i=1}^{n2} |V_{3i}| \qquad (11)$$

or $$w_1 \sum_{i=1}^{n} |V_{1i} + V_{PRF} - V_{2i}| + w_2 \sum_{i=1}^{n2} |V_{3i}|. \qquad (12)$$

A magnitude of total energy function (11) is compared with the magnitude of energy function (9). In some embodiments, the smaller magnitude is associated with the "correct" (i.e., non-aliased) color flow image. That is, FIG. 2A is assumed to be correct and non-aliased if the magnitude of energy function (9) is less than the magnitude of total energy function (11), otherwise the above-described corrected version of FIG. 2A is assumed to be correct.

In some embodiments, another total energy function may be calculated for the case of FIG. 2A as follows, $$\sum_{i=1}^{n} |V_{1i} - (V_{2i} - V_{PRF})| + \sum_{i=1}^{n2} |V_{3i} - V_{PRF}|, \qquad (13)$$

where the shades of red 214 ($V_{2i}$ and $V_{3i}$) are assumed to be aliased. As previously discussed, aliasing of positive velocities is corrected by subtracting $V_{PRF}$ from the aliased velocities. The total energy function (13) may be greater than the total energy functions (11) or (9). The comparison of three total energy function may yield the following result:

Energy function(11)<Energy function(9)<Energy function(13)

The total energy function (11) is smallest and therefore it is determined that its underlying assumption (i.e., the blue area is aliased) is correct. The assumptions behind energy functions (9), (11) and (13) may also or alternatively be evaluated by comparing weighted energy functions (10), (12) and (14).

$$w_1 \sum_{i=1}^{n} |V_{1i} - (V_{2i} - V_{PRF})| + w_2 \sum_{i=1}^{n2} |V_{3i} - V_{PRF}| \qquad (14)$$

Similarly, these assumptions may be evaluated using the power function (6), or the sum of the p-th power of the absolute differences of velocities (7). Moreover, the power function (6) or the sum of the p-th power of the absolute differences of velocity may be used in combination with weights to evaluate these assumptions. An example of the latter is as follows:

$$w_1 \sum_{i=1}^{n} |V_{1i} - (V_{2i} - V_{PRF})|^p + w_2 \sum_{i=1}^{n2} |V_{3i} - V_{PRF}|^p. \qquad (14\text{-}2)$$

The total energy function may indicate the velocity differences or gradients across the transitions. Flow or blood flow must follow physics or fluid mechanics laws. For example, flow velocity cannot change too rapidly spatial-wise, meaning velocity gradients or differences cannot be too large. FIG. 9A shows an example of velocities 905 measured by the color Doppler techniques. The horizontal axis is a spatial coordinate 910 (for example, a vessel diameter) and the vertical axis is the color Doppler velocity. At the left spatial point, the velocity 905 is virtually zero (0) and then increases gradually as the spatial point moves to the right until the velocity 905 reaches $0.5V_{PRF}$ and then suddenly changes to $-0.5V_{PRF}$. Then, the velocity 915 increases from $-0.5V_{PRF}$ to approximately $-0.2V_{PRF}$ and then decreases back to $-0.5V_{PRF}$. When the velocity 915 reaches $-0.5V_{PRF}$, it suddenly jumps back to $0.5V_{PRF}$.

FIG. 9A therefore represents a typical example of aliasing. There are two transitions 920, 925, from $0.5V_{PRF}$ to $-0.5V_{PRF}$ and from $-0.5V_{PRF}$ to $0.5V_{PRF}$. At the transitions 920, 925, the velocity differences are very large. If velocity is spatially continuously sampled, the velocity difference across the transition is $V_{PRF}$. The negative velocities 915 in FIG. 9A are all aliased. If this aliasing is corrected, the correct velocity distribution (profile) 955 may be obtained as shown in FIG. 9B. The velocity difference across the old transition is very small after aliasing correction, and may approach zero. FIGS. 9A and 9B show velocity distributions in one-dimension for simplicity. The determination of the smallest total energy function as discussed previously may represent searching for a solution for an optimal (most likely) 2-dimensional velocity distribution which does not exhibit aliasing.

Figure 2A:
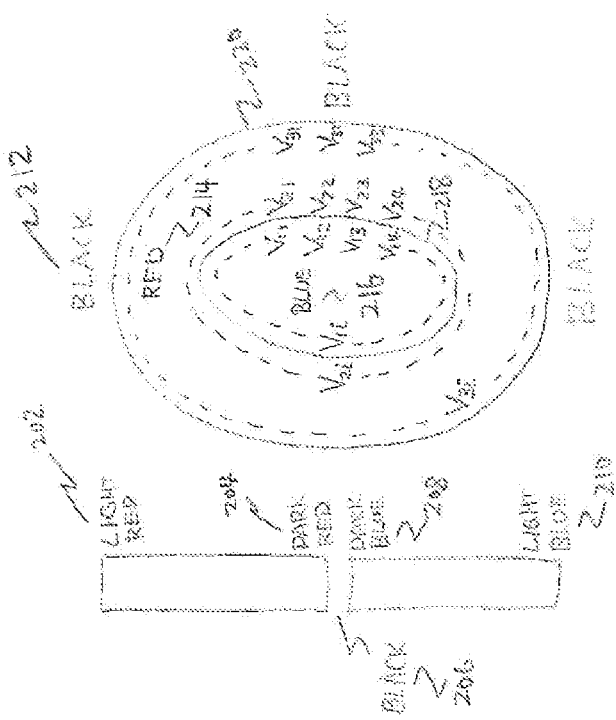
FIG. 2A: Color Doppler image with two flow areas.

A more complicated case is shown in FIG. 2B. In this example, the center area includes shades of red 268, indicating positive velocities, and is surrounded by a ring-like area of shades of blue 266, which in turn is surrounded by another ring-like area of shades of red 264, which is surrounded by black areas 262. Therefore, FIG. 2B illustrates three transitions 270, 272, 274. Velocities on one side of the first transition 270 are marked by $V_{11}, V_{12}, \ldots V_{1i}, \ldots$, while corresponding velocities on the other side of the first transition 270 are marked by $V_{21}, V_{22}, \ldots V_{2i}, \ldots$. An energy function across the first transition 270 is obtained as follows, $$\sum_{i=1}^{n} |V_{1i} - V_{2i}|, \qquad (15)$$

where n is the number of velocity samples.

Velocities on the blue-shaded side of the second transition 272 are marked by $V_{31}, V_{32}, \ldots V_{3i}, \ldots$, while the corresponding velocities of the red-shaded side of the second transition 272 are marked by $V_{41}, V_{42}, \ldots V_{4i}, \ldots$. An energy function across the second transition 272 is obtained as follows, $$\sum_{i=1}^{n2} |V_{3i} - V_{4i}|, \quad (16)$$

where n2 is the number of velocity samples.

Velocities on the red-shaded side of the third transition 274 are marked by $V_{51}, V_{52}, \ldots V_{5i}, \ldots$, while the black areas 262 represent zero velocities. A corresponding energy function for the third transition 274 is therefore obtained as follows, $$\sum_{i=1}^{n3} |V_{5i}|, \quad (17)$$

where n3 is the number of velocity samples.

The total energy function may be obtained as follows, $$\sum_{i=1}^{n} |V_{1i} - V_{2i}| + \sum_{i=1}^{n2} |V_{3i} - V_{4i}| + \sum_{i=1}^{n3} |V_{5i}|. \quad (18)$$

As described previously, various combinations of aliasing corrections may be applied to the velocity areas until the smallest total energy function is determined. All velocities of the same continuous flow area of a same velocity direction are corrected the same way, so if $V_{PRF}$ is added to a velocity of an area, $V_{PRF}$ is added to all other velocities in the same area.

Flow velocities may "wrap around" at the velocity limits (maximum velocity magnitude) more than once, in that they exceed the maximum velocity and the minimum velocity of the opposite velocity direction. FIGS. 11 and 12 illustrate such "double-aliasing", "triple-aliasing" and "quadruple-aliasing", in addition to the previously-described "single-aliasing". For example, positive velocities may exceed the positive maximum velocity 1175 and wrap around to the negative maximum velocity 1190 as shown by the dotted arrow 1120. The velocity range 1110 shows a true velocity range 1110. Once the aliasing occurs, the velocity range becomes "single-aliased" velocity range 1130 as shown in FIG. 11. The velocity then may further exceed zero velocity 1195 (or the negative minimum velocity 1185) and change the velocity direction again, resulting in positive velocities which may be called "double-aliased" velocities 1140. Then the velocity may further exceed the positive maximum velocity 1175 again and wrap around to the negative maximum velocity 1190 as shown by the dotted arrow 1150. The velocity may further increase in the "triple-aliased" velocity range 1160. The velocity then may further increase and go across the zero velocity 1195 and change the velocity direction, resulting in the positive velocities which may be called "quadruple aliased" velocities 1170. The above discussion of aliasing, "single-aliasing", "double-aliasing", "triple-aliasing", and "quadruple-aliasing" may also apply to the opposite direction as shown in FIG. 12.

For such aliasing, aliasing correction may include adding $V_{PRF}$ to the velocity if the "double-aliased" velocity is positive. If the double-aliased velocity is negative, $V_{PRF}$ is subtracted from the double-aliased velocity. Similarly, for "triple aliasing", $2V_{PRF}$ is subtracted from the triple-aliased velocity if the velocity is positive, and $2V_{PRF}$ is added to the triple-aliased velocity if the velocity is negative. For quadruple aliasing, $2V_{PRF}$ is added to the velocity if the velocity is positive, and $2V_{PRF}$ is subtracted from the velocity if the velocity is negative.

Aliasing corrections of various degrees (single aliasing, double aliasing, triple aliasing . . . ) may be applied to all or some of flow areas in FIG. 2B when determining the smallest total energy function (18). For example, the following function $$\sum_{i=1}^{n} |(V_{1i} + V_{PRF}) - (V_{2i} + V_{PRF})| + \sum_{i=1}^{n2} |(V_{3i} + V_{PRF}) - V_{4i}| + \sum_{i=1}^{n3} |V_{5i}| \quad (19)$$

may yield a lower value than (18). In this total energy function (19), the red center area 268 is assumed double-aliased, the blue ring-like area 266 is assumed single aliased and no aliasing is assumed in the red ring-like area 264. Weights ($w_1$, $w_2$, $w_3$) may be also associated with each energy function. The assumptions behind functions (18) and (19) may also be evaluated using the power function, or the sum of the p-th power of the absolute differences of velocities. The same aliasing corrections are applied to all velocities of a continuous flow area of the same velocity direction (i.e., positive or negative) when the total energy function is calculated. For example, $V_{PRF}$ is added to all velocities inside the blue-ring area including $V_{21}, V_{22}, \ldots V_{2i}, \ldots$ and $V_{31}, V_{32}, \ldots V_{3i}, \ldots$.

Figure 10:
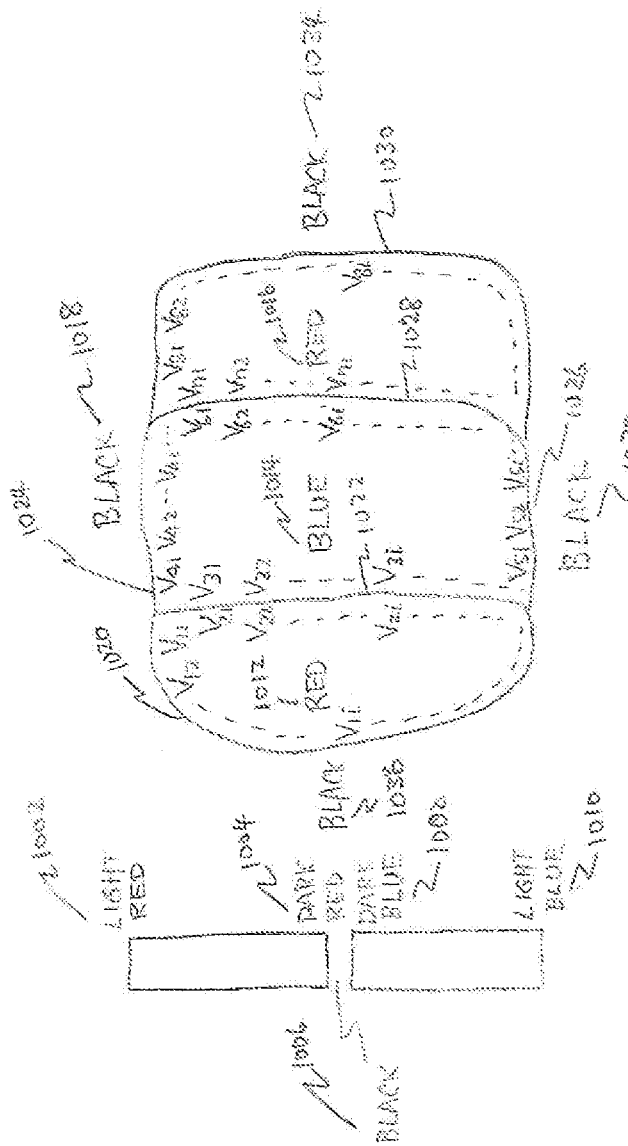
FIG. 10: Color Doppler image with three flow areas.

FIG. 10 illustrates a color flow image in which flow areas are divided into three areas of red shades 1012, blue shades 1014 and red shades 1016. The image includes a first transition 1020 between the black area 1036 (i.e., zero velocity) and the left-most red-shaded area 1012. Velocities adjacent to this transition are marked by $V_{11}, V_{12}, \ldots V_{1i}, \ldots$ while the black area 1036 may have zero velocities. For this transition 1020, an energy function may be obtained as follows, $$\sum_{i=1}^{n} |V_{1i}|, \quad (20)$$

where n is the number of velocity samples.

The second transition 1022 is between the left-most red-shaded area 1012 and the blue-shaded area 1014. Velocities on the red-shaded side of the transition 1022 are marked by $V_{21}, V_{22}, \ldots V_{2i}, \ldots$, while the corresponding velocities on the blue-shaded side of the transition 1022 are marked by $V_{31}, V_{32}, \ldots V_{3i}, \ldots$. For this transition 1022, an energy function may be obtained as follows, $$\sum_{i=1}^{n2} |V_{2i} - V_{3i}|, \quad (21)$$

where n2 is the number of velocity samples.

A third transition 1024 exists between the blue-shaded area 1014 and a black area 1018 at the top of the color flow image. Velocities on the blue-shaded side of the transition 1024 are marked by $V_{41}, V_{42}, \ldots V_{4i}, \ldots$ while the black area may have zero velocities. For this transition 1024, an energy function may be obtained as follows, $$\sum_{i=1}^{n3} |V_{4i}|, \quad (22)$$

where n3 is the number of velocity samples.

The fourth transition 1026 is between the blue-shaded area 1014 and a black area 1032 at the bottom of the color flow image. Velocities on the blue-shaded side of the transition 1026 are marked by $V_{51}, V_{52}, \ldots V_{5i}, \ldots$ while the black area 1032 may have zero velocities. For this transition 1026, an energy function may be obtained as follows, $$\sum_{i=1}^{n4} |V_{5i}|, \quad (23)$$

where n4 is the number of velocity samples.

A fifth transition 1028 exists between the blue-shaded area 1014 and the right-most red-shaded area 1016. Velocities on the blue-shaded side of the transition 1028 are marked by $V_{61}, V_{62}, \ldots V_{6i}, \ldots$ while velocities on the red-shaded side of the transition 1028 are marked by $V_{71}, V_{72}, \ldots V_{7i}, \ldots$. For this transition 1028, an energy function may be obtained as follows, $$\sum_{i=1}^{n5} |V_{6i} - V_{7i}|, \quad (24)$$

where n5 is the number of velocity samples.

The sixth transition 1030 is between the right-most red-shaded area 1016 and the black area 1034. Velocities on the red-shaded side of the transition 1030 are marked by $V_{81}, V_{82}, \ldots V_{8i}, \ldots$ while the black area 1034 may have zero velocities. For this transition 1030, an energy function may be obtained as follows, $$\sum_{i=1}^{n6} |V_{8i}|, \quad (25)$$

where n6 is the number of velocity samples.
The total energy function may be obtained as follows, $$\sum_{i=1}^{n} |V_{1i}| + \sum_{i=1}^{n2} |V_{2i} - V_{3i}| + \qquad (26)$$
$$\sum_{i=1}^{n3} |V_{4i}| + \sum_{i=1}^{n4} |V_{5i}| + \sum_{i=1}^{n5} |V_{6i} - V_{7i}| + \sum_{i=1}^{n6} |V_{8i}|$$

and aliasing corrections may be introduced to all or some of the flow areas as discussed previously. The same aliasing corrections are applied to all velocities inside the transitions or to all velocities of a same continuous flow area of a same velocity direction when calculating the total energy function. Aliasing corrections may be applied to black areas which represent zero velocities if aliasing is not involved. For example, $V_{PRF}$ may be added to $V_{31}, V_{32}, \ldots V_{3i}, \ldots$ and $V_{41}, V_{42}, \ldots V_{4i}, \ldots$ and $V_{51}, V_{52}, \ldots V_{5i}, \ldots$ and $V_{61}, V_{62}, \ldots V_{6i}, \ldots$ for the case of FIG. 10. As described above, those aliasing corrections which result in a smallest total energy function are considered to reflect the true flow velocity conditions. The degree of aliasing correction may be infinite or may be limited to a finite degree, e.g., no aliasing, single aliasing, double aliasing, triple aliasing, and quadruple aliasing, meaning (i.e., respectively, 0, $V_{PRF}$, $-V_{PRF}$, $2V_{PRF}$, and $-2V_{PRF}$).

Figure 13:
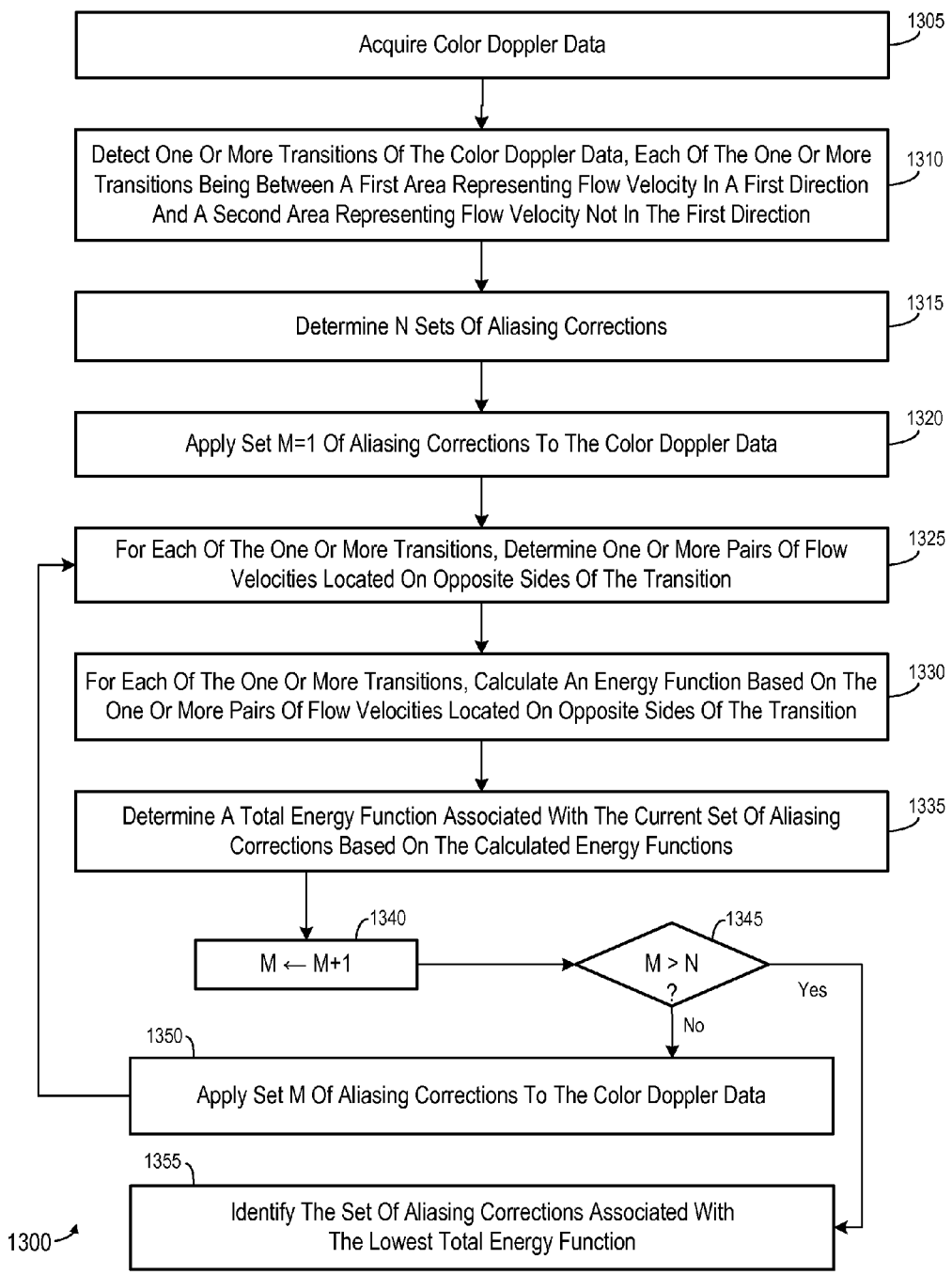
FIG. 13: A flow diagram of a process to address aliasing correction according to some embodiments.

FIG. 13 is a flow diagram of a process 1300 to describe the aliasing correction method previously discussed. First, color Doppler data including color flow lines or color Doppler images may be acquired at 1305. One or more transitions in the color Doppler data are detected at 1310. The one or more transitions may include transitions between a positive flow velocity area and a negative flow velocity area, between a negative flow velocity area and a zero flow velocity area, and/or between a positive flow velocity area and a zero flow velocity area.

Several (e.g., N=a positive integer) sets of aliasing corrections are determined at 1315. A set of aliasing corrections includes one aliasing correction (e.g., $0V_{PRF}$, $+/-V_{PRF}$, $+/-2V_{PRF}$, $+/-3V_{PRF}$, $+/-4V_{PRF}$, $+/-5V_{PRF}$) to be applied to color Doppler data within each of the detected transitions.

When determining the N sets of aliasing corrections, the maximum degree of aliasing and its correction is limited to save computation time. All possible combinations of flow areas and degree of aliasing (e.g. no aliasing, single aliasing and to up to the maximum degree of aliasing) are considered in the determination of the aliasing correction sets. As will be described below, a total energy function is determined for each one of the determined sets of aliasing corrections.

In some embodiments, the possible sets of aliasing corrections may include only particular degrees of aliasing correction (e.g., no aliasing to quadruple aliasing or $0V_{PRF}$, $+/-V_{PRF}$, $+/-2V_{PRF}$) in order to reduce processing workload.

A first set of aliasing corrections (i.e., M=1) is applied to the acquired color Doppler data at 1320. The first set of aliasing corrections may include no aliasing corrections, so that the "corrected" color Doppler data is identical to the originally-acquired color Doppler data.

For each transition, one or more pairs of flow velocities located on opposite sides of the transition are located at 1325. Next, and also for each transition, an energy function is calculated at 1330 based on the one or more pairs of flow velocities (or color Doppler values, i.e., the Doppler shift frequency or the color Doppler phase) located on opposite sides of the transition. As described above, this calculation may be based on the sum of the absolute differences of the one or more pairs of flow velocities located on opposite sides of the transition.

According to some embodiments, the number of flow velocities on each side of the transition need not be identical. Consequently, a same flow velocity on a side of the transition may belong to more than one of the one or more pairs of flow velocities. For example, with respect to FIG. 2B, calculation of an energy function at 1330 may include determination of an absolute difference between flow velocity pair ($V_{31}$, $V_{41}$) and of an absolute difference between flow velocity pair ($V_{31}$, $V_{42}$).

A total energy function associated with the first set of aliasing corrections is determined at 1335. In some embodiments, the total energy function is the sum of all the energy functions determined for all the transitions and for the first set of aliasing corrections. Determination of the total energy function at 1335 may include weighting one or more of the individual energy functions as described previously.

1340 and 1345 are intended to simply describe selection of a next set of aliasing corrections, if any, from the determined N sets of aliasing corrections. Embodiments are not limited to the specific mechanisms described with respect to 1340 and 1345. In particular, at 1340, a counter (i.e., M) representing the previously-applied set of aliasing corrections is incremented by one (i.e., M←M+1) to indicate a next set of aliasing corrections. If it is determined at 1345 that the value of the counter is greater than N, then a respective total energy function has been determined for each of the determined N sets of aliasing corrections. If not, the next set of aliasing corrections is applied to the originally-acquired color Doppler data at 1350 and flow returns to 1325 to determine one or more pairs of "corrected" flow velocities for each transition and to calculate an energy function for each transition at 1330.

Flow continues as described above to determine a total energy function associated with the latest set of aliasing corrections at 1335. This loop repeats to determine a total energy function associated with each candidate set of aliasing corrections, until it is determined at 1345 that no more sets of aliasing corrections are to be evaluated because M is greater than N(M>N).

Flow then proceeds to 1355 to identify a set of aliasing corrections associated with the lowest total energy function. According to some embodiments, this identified set of aliasing corrections is assumed to be correct, and is therefore applied to the originally-acquired color Doppler data in order to correct any aliasing exhibited thereby.

Figure 6B:
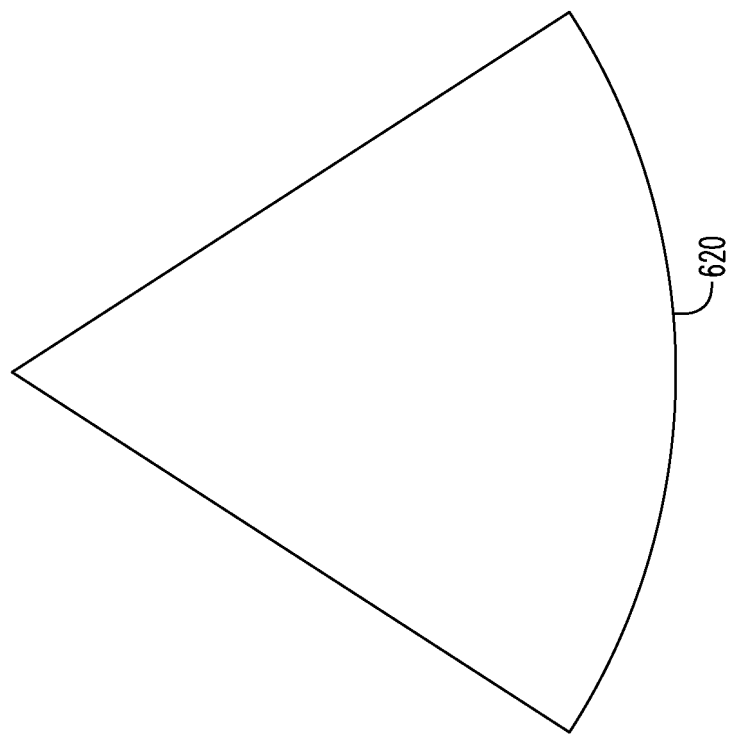
FIG. 6B: A representation of a scan-converted color flow image.
Figure 6A:
FIG. 6A: A representation of color flow lines.
Figure 7B:
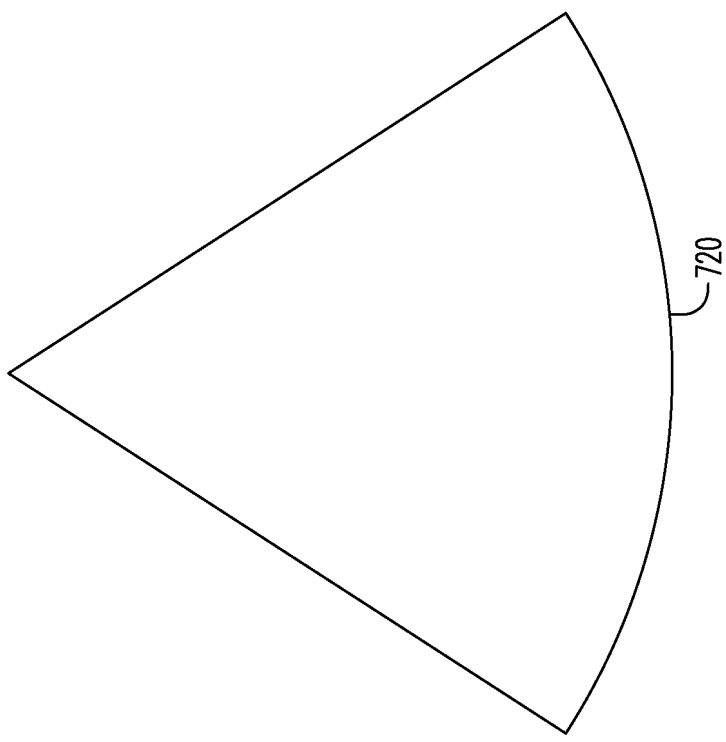
FIG. 7B: A representation of a scan-converted B-mode image.
Figure 7A:
FIG. 7A: A representation of B-mode lines.

Moreover, embodiments are not limited to the above description of process 1300, and the steps of process 1300 may be performed in any order that is practicable. As mentioned above, the method may be applied to color flow line data or color Doppler image data according to some embodiments. FIG. 6A shows color flow lines 600 before scan-conversion, although only 11 lines are shown as an example. A color flow line consists of many color flow data samples along the line. Color flow lines 600 are created from color beam data and may not show correct spatial dimensions. Scan-conversion is a technique to convert the color flow lines to a raster video image by interpolating the color flow lines. In a scan-converted image 620 (e.g., sector scan) shown FIG. 6B, the color flow image consists of color flow image pixels of the orthogonal (x-y) coordinate with the correct length relationship (vertical vs. horizontal dimensions) in contrast to the color flow lines 600 shown in FIG. 6A. B-mode imaging also uses the scan-conversion technique to convert B-mode lines 700 as shown in FIG. 7A to a B-mode image 720 as shown in FIG. 7B by interpolating B-mode line data 700.

Figure 3:
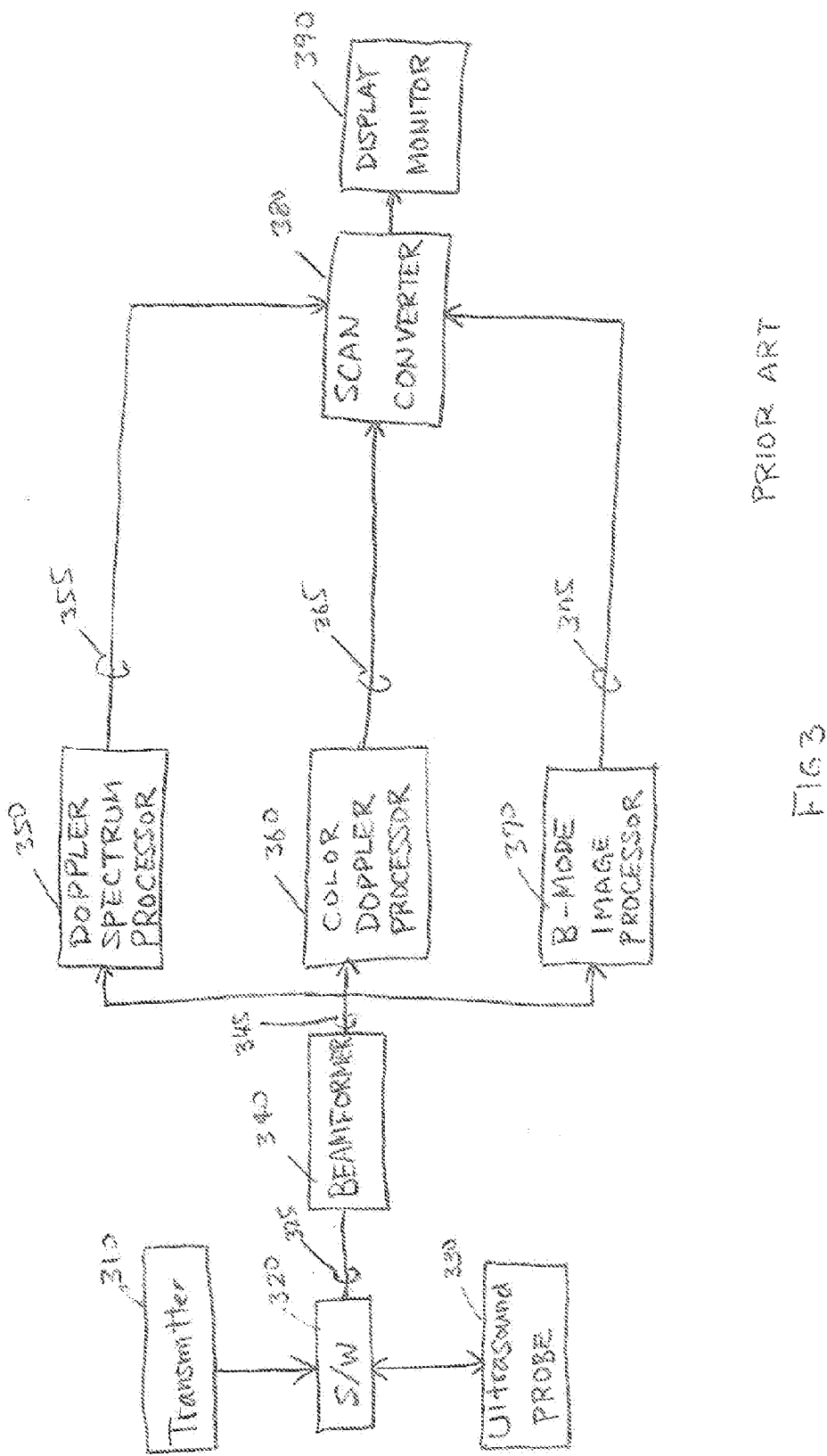
FIG. 3: A diagram of an ultrasound diagnostic imaging system (prior art).

FIG. 3 shows a diagram of a conventional ultrasound diagnostic imaging system with B-mode imaging, Doppler spectrum and color Doppler imaging (e.g., see U.S. Pat. No. 4,573,477, U.S. Pat. No. 4,622,977, U.S. Pat. No. 4,641,668, U.S. Pat. No. 4,651,742, U.S. Pat. No. 4,651,745, U.S. Pat. No. 4,759,375, U.S. Pat. No. 4,766,905, U.S. Pat. No. 4,768,515, U.S. Pat. No. 4,771,789, U.S. Pat. No. 4,780,837, U.S. Pat. No. 4,799,490, and U.S. Pat. No. 4,961,427). The system may include other imaging modes, e.g. elasticity imaging, 3D imaging, real-time 3D imaging, tissue Doppler imaging, tissue harmonic imaging, contrast imaging and others. An ultrasound signal is transmitted from an ultrasound probe 330 driven by a transmitter 310 through a transmit/receive switch 320. The probe 320 may consist of an array of transducer elements which are separately driven by the transmitter with different time-delays so that a transmit ultrasound beam is focused and steered. A beamformer 340 receives the received ultrasound signal(s) from the probe 330 through the switch 320 and processes the signal(s) 325. The beamformer applies delays and/or phases to the signals and the resultant signals are summed for focusing and steering a receive ultrasound beam. The beamformer may also apply apodization, amplification and filtering.

The processed signal 345 is coupled to a Doppler spectrum processor 350, a color Doppler processor 360, and a B-mode image processor 370. The Doppler spectrum processor 350 includes a Doppler signal processor and a spectrum analyzer, and processes Doppler flow velocity signals and calculates and outputs a Doppler spectrum 355. The color Doppler processor 360 processes the received signal 345 and calculates and outputs velocity, power and variance signals 365. The B-mode image processor 370 processes the received signal 345 and calculates and outputs a B-mode image 375 or the amplitude of the signal by an amplitude detection.

The Doppler spectrum signals 355, color Doppler processor signals (velocity, power, and variance) 365 and B-mode processor signals 375 are coupled to a scan converter 380 that converts the signals to scan-converted signals. The output of scan converter 380 is coupled to a display monitor 390 for displaying ultrasound images.

Figure 4:
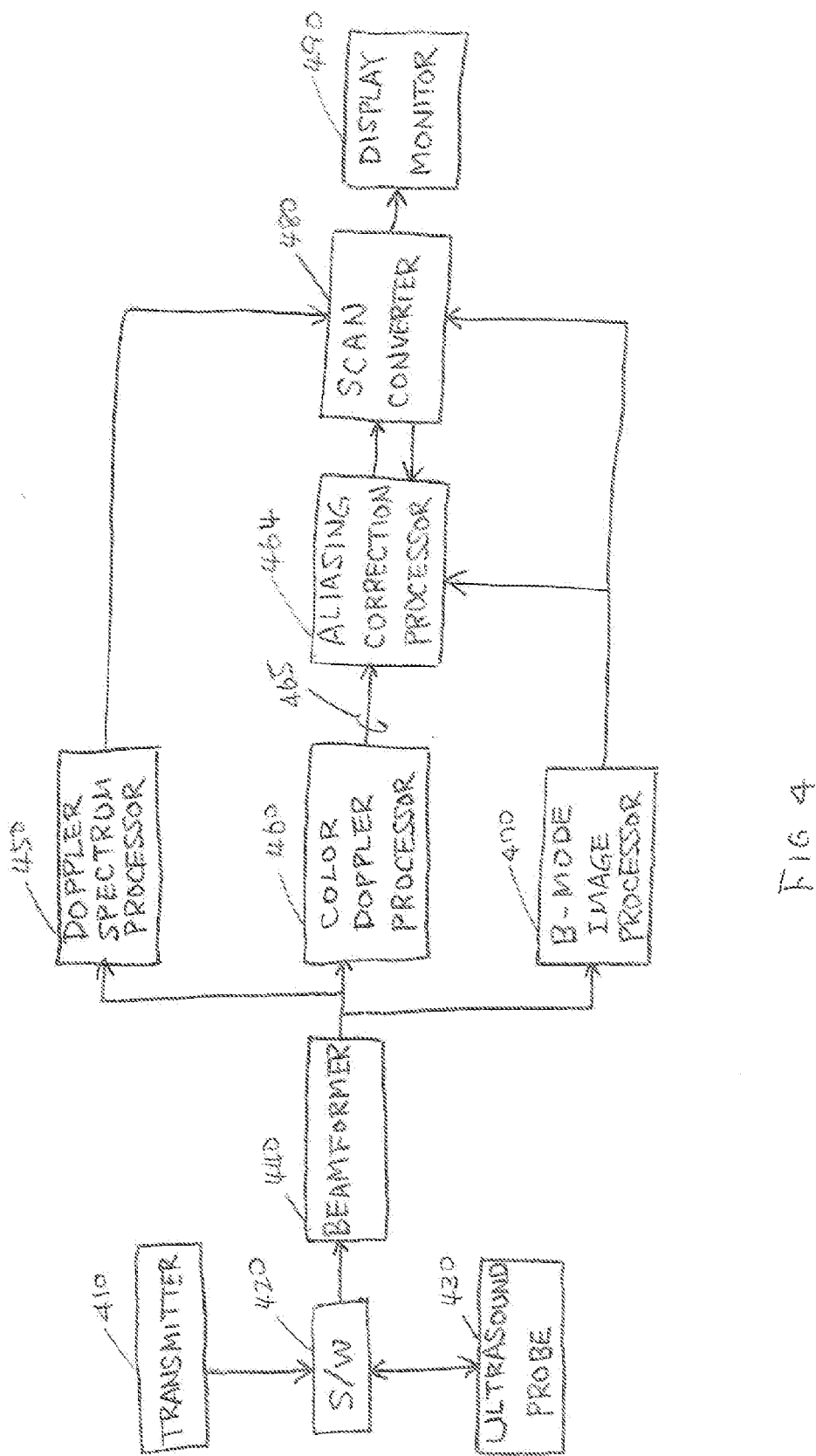
FIG. 4: A diagram of an ultrasound diagnostic imaging system according to some embodiments and using line data.
Figure 5:
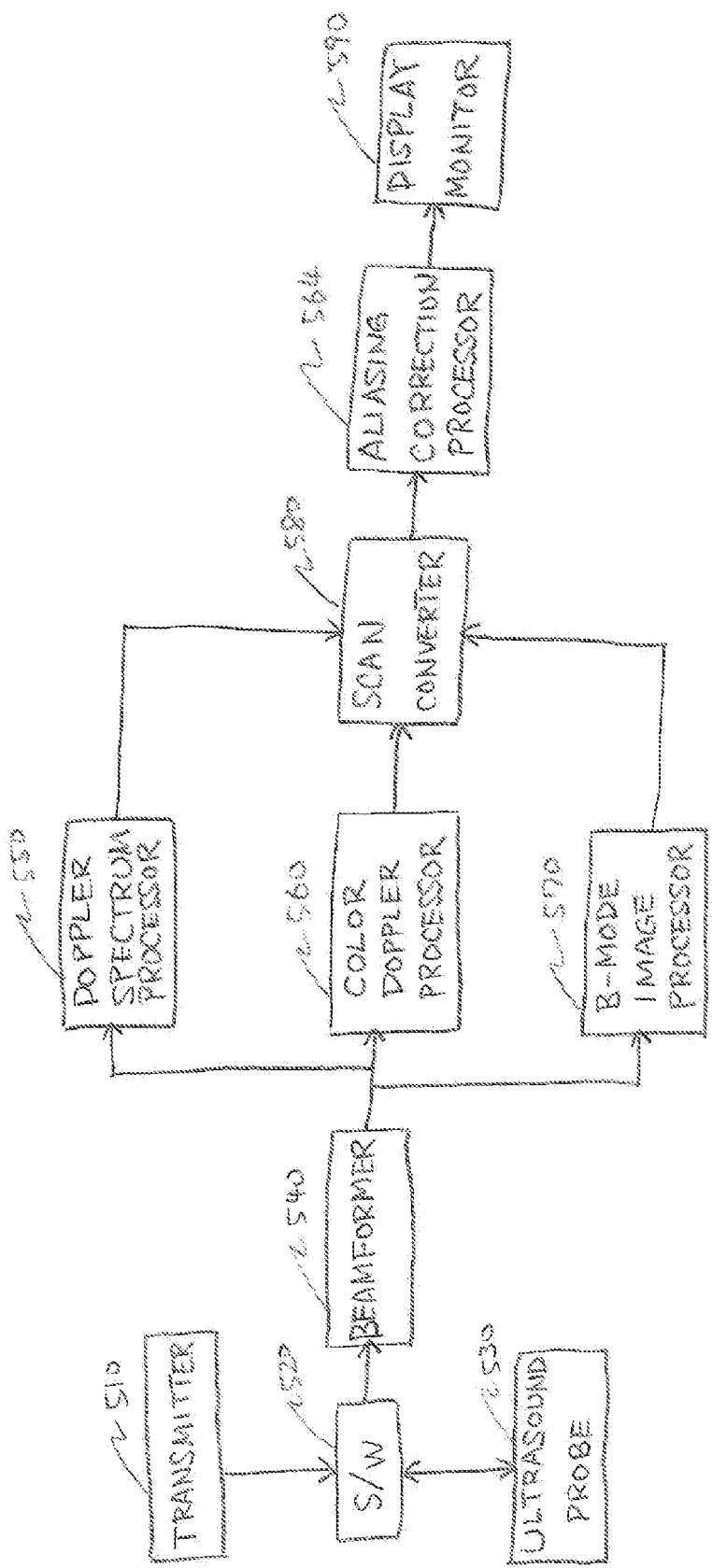
FIG. 5: A diagram of an ultrasound diagnostic imaging system according to some embodiments and using scan-converted images.

FIG. 4 shows a diagram of an ultrasound imaging system including a color Doppler aliasing correction processor 464 according to some embodiments. The aliasing correction processor 464 may perform the aliasing correction method described previously with respect to color flow line data as described above. The aliasing correction processor 464 receives output 465 from the color Doppler processor 460. Output 465 comprises color flow line data rather than the scan-converted color Doppler image. The aliasing correction processor 464 outputs correct color Doppler data after aliasing correction. FIG. 5 shows a diagram of embodiments in which the correction of color Doppler aliasing is performed in the scan-converted image domain rather than the line data domain which was discussed previously. The B-mode image and color Doppler image are scan-converted before the aliasing correction processor 564 performs processing thereon.

The aliasing correction processors 464, 564 may be comprised of general purpose central processing units (CPUs), digital signal processors (DSPs), field programmable Arrays (FPGAs), graphic processing units (GPUs) and/or discreet electronics devices.

The foregoing description references velocity, velocity aliasing and velocity aliasing corrections. However, the description may be equally applicable to the frequency domain or the phase domain via equations (1), (3) and (4). The velocity or color velocity, which is actually the velocity component v cos θ in the ultrasound beam direction as shown in equation (1), may be converted to the Doppler shift frequency via equation (1). Then, the Doppler shift frequency in turn may be converted to a phase or the color Doppler phase via equation (4). Velocity aliasing may be converted to frequency aliasing or phase aliasing. Aliasing correction may be applied to Doppler shift frequency values in the frequency domain or color Doppler phase values in the phase domain.

Color velocity, color flow velocity, color Doppler velocity, flow velocity or velocity discussed herein are directly related to the Doppler shift frequency via equation (1) and are actually the flow velocity component in the ultrasound beam direction as implied by cos θ or the projection of the true flow velocity onto the ultrasound beam direction assuming no aliasing.

The positive velocity or positive velocity direction refers to a flow that is directed toward the ultrasound transducer within a range of +/−90 degrees from the center axis of the ultrasound beam rather than away from the transducer. The negative velocity or negative velocity direction refers to flow directed away from the ultrasound transducer with a range of +/−90 degrees from the center axis of ultrasound beam.

The foregoing description is made with the aid of two-dimensional images or figures to describe transitions and flow areas. However, the transitions and flow areas may be three-dimensional or two-dimensional without imposing any limitations.

One or more embodiments have been described. Nevertheless, various modifications will be apparent to those in the art.

What is claimed is:

1. A method implemented by an imaging system, comprising:
    acquiring color Doppler data;
    detecting one or more transitions of the color Doppler data, each of the one or more transitions being between a first area representing flow velocity in a first direction and a second area representing flow velocity not in the first direction;
    applying a first set of aliasing corrections to the color Doppler data to generate second color Doppler data;
    for each of the one or more transitions, determining one or more pairs of color Doppler values in the second color Doppler data, wherein each color Doppler value of a pair of color Doppler values is located on opposite sides of a transition;
    for each of the one or more transitions, evaluating a first energy function based on the one or more pairs of color Doppler values in the second color Doppler data, wherein each color Doppler value of a pair of color Doppler values is located on opposite sides of a transition;
    determining a first total energy function associated with the first set of aliasing corrections based on the evaluated first energy functions;
    applying a second set of aliasing corrections to the color Doppler data to generate third color Doppler data;
    for each of the one or more transitions, determining one or more pairs of color Doppler values in the third color Doppler data, wherein each color Doppler value of a pair of color Doppler values is located on opposite sides of a transition;
    for each of the one or more transitions, evaluating a second energy function based on the one or more pairs of color Doppler values in the third color Doppler data, wherein each color Doppler value of a pair of color Doppler values is located on opposite sides of a transition;
    determining a second total energy function associated with the second set of aliasing corrections based on the evaluated second energy functions;
    determining whether the first total energy function is less than the second total energy function or whether the second total energy function is less than the first total energy function; and
    identifying the first set of aliasing corrections as a correct set of aliasing corrections if the first total energy function is less than the second total energy function, and identifying the second set of aliasing corrections as the correct set of aliasing corrections if the second total energy function is less than the first total energy function.

2. A method according to claim 1, wherein the acquired color Doppler data comprises color flow line data or scan-converted color flow image data.

3. A method according to claim 1, wherein the acquired color Doppler values comprise color flow velocities, Doppler shift frequencies or color Doppler phases.

4. A method according to claim 1, wherein evaluation of the first energy function for a transition comprises:
    calculation of the sum of the absolute differences between each of the one or more pairs of color Doppler values, wherein each color Doppler value of a pair of color Doppler values is located on opposite sides of the transition.

5. A method according to claim 1, wherein evaluation of the first energy function for a transition comprises:
    calculation of the sum of the p-th power of the absolute differences between each of the one or more pairs of color Doppler values, wherein each color Doppler value of a pair of color Doppler values is located on opposite sides of the transition.

6. A method according to claim 1, wherein evaluation of the first total energy function comprises:
    multiplying each of the first energy functions by a respective weight to obtain a respective product; and
    adding the respective products.

7. A method according to claim 1, wherein the first set of aliasing corrections comprise one or more of 0, $f_{PRF}$, $-f_{PRF}$, $2f_{PRF}$, $-2f_{PRF}$, $3f_{PRF}$, $-3f_{PRF}$, $4f_{PRF}$, $-4f_{PRF}$, $5f_{PRF}$ and $-5f_{PRF}$ of the Doppler shift frequency or
    one or more of 0, $V_{PRF}$, $-V_{PRF}$, $2V_{PRF}$, $-2V_{PRF}$, $3V_{PRF}$, $-3V_{PRF}$, $4V_{PRF}$, $-4V_{PRF}$, $5V_{PRF}$ and $-5V_{PRF}$ of color Doppler velocity or
    one or more of 0, $2\pi$, $-2\pi$, $4\pi$, $-4\pi$, $6\pi$, $-6\pi$, $8\pi$, $-8\pi$, $10\pi$ and $-10\pi$ of the color Doppler phase.

8. A method according to claim 1, wherein the first total energy function associated with the first set of aliasing corrections is determined by summing the evaluated first energy functions.

9. A method according to claim 1, wherein the second total energy function associated with the second set of aliasing corrections is determined by summing the evaluated second energy functions.

10. A system comprising:
    an aliasing correction processor to:
    acquire color Doppler data;
    detect one or more transitions of the color Doppler data, each of the one or more transitions being between a first area representing flow velocity in a first direction and a second area representing flow velocity not in the first direction;
    apply a first set of aliasing corrections to the color Doppler data to generate second color Doppler data;
    for each of the one or more transitions, determine one or more pairs of color Doppler values in the second color Doppler data, wherein each color Doppler value of a pair of color Doppler values is located on opposite sides of a transition;
    for each of the one or more transitions, evaluate a first energy function based on the one or more pairs of color Doppler values in the second color Doppler data, wherein each color Doppler value of a pair of color Doppler values is located on opposite sides of a transition;
    determine a first total energy function associated with the first set of aliasing corrections based on the evaluated first energy functions;
    apply a second set of aliasing corrections to the color Doppler data to generate third color Doppler data;
    for each of the one or more transitions, determine one or more pairs of color Doppler values in the third color Doppler data, wherein each color Doppler value of a pair of color Doppler values is located on opposite sides of a transition;

for each of the one or more transitions, evaluate a second energy function based on the one or more pairs of color Doppler values in the third color Doppler data, wherein each color Doppler value of a pair of color Doppler values is located on opposite sides of a transition;

determine a second total energy function associated with the second set of aliasing corrections based on the evaluated second energy functions;

determine whether the first total energy function is less than the second total energy function or whether the second total energy function is less than the first total energy function; and identify the first set of aliasing corrections as a correct set of aliasing corrections if the first total energy function is less than the second total energy function, and identify the second set of aliasing corrections as the correct set of aliasing corrections if the second total energy function is less than the first total energy function.

11. A system according to claim 10, further comprising a color Doppler processor to provide the color Doppler data to the aliasing correction processor, wherein the acquired color Doppler data comprises color flow line data or scan-converted color flow image data.

12. A system according to claim 10, wherein the acquired color Doppler values comprise color flow velocities, Doppler shift frequencies or color Doppler phases.

13. A system according to claim 10, wherein evaluation of the first energy function for a transition comprises:

calculation of the sum of the absolute differences between each of the one or more pairs of color Doppler values, wherein each color Doppler value of a pair of color Doppler values is located on opposite sides of the transition.

14. A system according to claim 10, wherein evaluation of the first energy function for a transition comprises:

calculation of the sum of the p-th power of the absolute differences between each of the one or more pairs of color Doppler values, wherein each color Doppler value of a pair of color Doppler values is located on opposite sides of the transition.

15. A system according to claim 10, wherein evaluation of the first total energy function comprises:

multiplication of each of the first energy functions by a respective weight to obtain a respective product; and addition of the respective products.

16. A system according to claim 10, wherein the first set of aliasing corrections comprise one or more of $0, V_{PRF}, -V_{PRF}, 2V_{PRF}, -2V_{PRF}, 3V_{PRF}, -3V_{PRF}, 4V_{PRF}, -4V_{PRF}, 5V_{PRF}$ and $-5V_{PRF}$ of the color flow velocity or one or more of $0, f_{PRF}, -f_{PRF}, 2f_{PRF}, -2f_{PRF}, 3f_{PRF}, -3f_{PRF}, 4f_{PRF}, -4f_{PRF}, 5f_{PRF}$ and $-5f_{PRF}$ of the Doppler shift frequency or one or more of $0, 2\pi, -2\pi, 4\pi, -4\pi, 6\pi, -6\pi, 8\pi, -8\pi, 10\pi$ and $-10\pi$ of the color Doppler phase.

17. A system according to claim 10, wherein the first total energy function associated with the first set of aliasing corrections is determined by summing the evaluated first energy functions.

18. A system according to claim 10, wherein the second total energy function associated with the second set of aliasing corrections is determined by summing the evaluated second energy functions.

* * * * *